US007202369B2

United States Patent
Baik et al.

(10) Patent No.: US 7,202,369 B2
(45) Date of Patent: Apr. 10, 2007

(54) PROCESSES FOR PREPARING OF 3,4-ALKYLENEDIOXYTHIOPHENES AND 3,4-DIALKOXYTHIOPHENES

(75) Inventors: Woon-Phil Baik, 10 Myongji Village, San 33-1, Nam-dong Yongi-si, Gyeonggi-do (KR); Young-Sam Kim, Gyeonggi-do (KR); Hee-Jung Hong, Seoul (KR); Sang-Gook Jung, Gyeonggi-do (KR)

(73) Assignee: Woon-Phil Baik, Gyeonggi-do (KR)

( * ) Notice: Subject to any disclaimer, the term of this patent is extended or adjusted under 35 U.S.C. 154(b) by 388 days.

(21) Appl. No.: 10/715,845

(22) Filed: Nov. 19, 2003

(65) Prior Publication Data

US 2004/0147765 A1    Jul. 29, 2004

(30) Foreign Application Priority Data

Nov. 19, 2002    (KR) ...................... 10-2002-0071992

(51) Int. Cl.
*C07D 495/02*    (2006.01)
*C07D 333/00*    (2006.01)

(52) U.S. Cl. .............................. 549/50; 549/29; 549/49
(58) Field of Classification Search .................. 549/29, 549/49, 50
See application file for complete search history.

(56) References Cited

U.S. PATENT DOCUMENTS

| 2,453,103 | A | 11/1948 | Turnbull, Jr. |
| 6,369,239 | B2 | 4/2002 | Rauchschwalbe et al. |
| 6,528,662 | B2 * | 3/2003 | Jonas .......................... 549/50 |
| 6,750,354 | B2 * | 6/2004 | Rauchschwalbe et al. .... 549/60 |

* cited by examiner

*Primary Examiner*—Golam M. M. Shameem
(74) *Attorney, Agent, or Firm*—Nixon & Vanderhye P.C.

(57) ABSTRACT

The present invention relates to a process for preparing 3,4-dialkoxythiophenes or 3,4-alkylenedioxythiophenes in high yield via the rapid decarboxylation of 3,4-dialkoxythiophenedicarboxylic acid or 3,4-aklylenedioxythiophenedicarboxylic acid in a water-miscible polar solvent in the presence of copper catalyst under an oxygen atmosphere.

9 Claims, No Drawings

PROCESSES FOR PREPARING OF 3,4-ALKYLENEDIOXYTHIOPHENES AND 3,4-DIALKOXYTHIOPHENES

FIELD OF THE INVENTION

The present invention relates to a process for preparing of 3,4-dialkoxythiophenes and 3,4-alkylenedioxythiophenes. More specifically, it relates to a process for preparing of 3,4-dialkoxythiophenes and 3,4-alkylenedioxythiophenes in high purity by the decarboxylation of 3,4-dialkoxythiophenedicarboxylic acid and 3,4-alkylenedioxythiophenedicarboxylic acid, respectively, in a water-miscible polar solvent in the presence of copper catalyst under an oxygen atmosphere.

BACKGROUND OF THE INVENTION

This invention relates to a process for preparing of 3,4-dialkoxythiophenes and 3,4-alkylenedioxythiophenes by the decarboxylation of 3,4-dialkoxythiophenedicarboxylic acid and 3,4-alkylenedioxythiophenedicarboxylic acid, respectively, in a water-miscible polar solvent in the presence of copper catalyst under an oxygen atmosphere. As conductive polymers, polyanilines, polypyrroles and polythiophenes are used in various applications of electronic materials. In particular, polythiophenes have excellent physical properties.

Among them, poly(3,4-alkylenedioxythiophene) in which substituent(s) are introduced at the 3,4-position of the thiophene ring to improve solubility, thermal stability and chemical(solvent) resistance, has been developed by Bayer, Germany, and is used in various fields. Poly(3,4-alkylenedioxythiophene) can be used as 1) an antistatic agent;
2) an alternative to electrolytes in a condenser;
3) a coating on a printed circuit board; and
4) a hole-injecting layer in an organic electro-luminescence device.

Poly(3,4-alkylenedioxythiophene) is generally prepared from the monomer 3,4-alkylenedioxythiophene. Thus, methods for synthesizing the monomer 3,4-alkylenedioxythiophene are also very important. The synthesis for a representative derivative, 3,4-ethylenedioxythiophene (EDOT), consists of four steps (step 1: condensation/step 2: substitution/step 3: hydrolysis/step 4: decarboxylation) starting from thiodiglycolate, as shown in Reaction Scheme (1):

Reaction Scheme 1

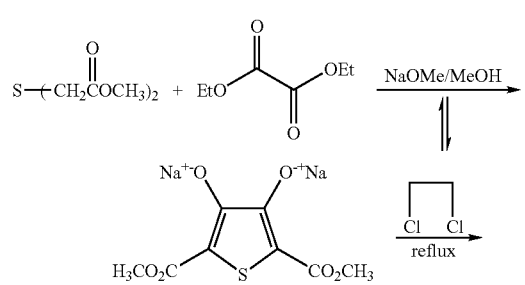

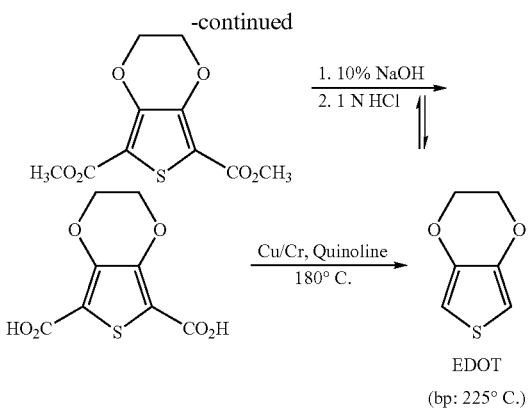

Steps 1, 2 and 3 are general reactions that present no difficulties. On the other hand, step 4 (decarboxylation) should be improved because it has many shortcomings, including a low yield, complicated purification process, use of expensive solvent, and a high reaction temperature.

The method for the decarboxylation of 3,4-dialkoxythiophenedicarboxylic acid or 3,4-alkylenedioxythiophenedicarboxylic acid described by U.S. Pat. No. 2,453,103 (1948), E. Fager, [*J. Amer. Chem. Soc.,* 1945, 67, 2217–8] and M. coffey et al., *[Synth. Commun.,* 1996, 26, 2205–12] is generally carried out in the presence of copper catalyst (or Cu/Cr oxide) and quinoline solvent at high temperature (180~200° C.) under a nitrogen atmosphere.

The general drawbacks of these prior arts can be summarized as follows:

1) The boiling point of quinoline is 238° C., while the boiling point of the final product (EDOT) is 225° C., and thus the product can not be isolated by fractional distillation. Instead, it must be isolated or purified by column chromatography, which is a drawback on an industrial scale.

2) The solvent quinoline should be avoided since it interferes with the workup process. Workup is carried out by washing with water and acid. The quinoline salt enters the waste-water, where it then causes environmental pollution or adds an additional step to recover the quinoline salt from the aqueous phase.

3) Since the reaction is carried out at high temperature (not lower than 180° C.) for a long period of time, substantial impurities such as tar-like materials are formed to give a bad yield (60% or less) or difficulties in purification.

According to E. Fager [*J. Am. Chem. Soc.,* 1951, 2956–57], decarboxylation is performed by thermal decomposition at 190° C. in the presence of copper powder without solvent in vacuo (20~40 mmHg), so that 3,4-dimethoxythiophene is prepared after distillation. This reaction is inappropriate for an industrial scale because it requires a considerable expenditure of energy and special equipment. A process for preparing 3,4-dimethoxythiophene from 3,4-dimethoxythiophenedicarboxylic acid by decarboxylation at high temperature (250° C.) without solvent or catalyst has also been reported [*J. Prakt. Chem.,* 1996, 672–4], however, the yield is less than 65%.

U.S. Pat. No. 6,369,239 (2002) describes a process for preparing 3,4-dialkoxythiophenes or 3,4-alkylenedioxythiophenes by the decarboxylation of 3,4-dialkoxythiophenedicarboxylic acids or 3,4-alkylenedioxythiophenedicarboxylic acids, respectively, in the presence of high-boiling-point (230° C. or higher) solvent and copper salt catalyst (or no catalyst) under a nitrogen atmosphere.

According to this process, decarboxylation is performed without catalyst by heating at 240° C. or higher for 24 hours, or in the presence of high-boiling-solvent and copper salt catalyst at 140° C. for 8 hours or more, and, similar to the prior arts it also gives a tar-like byproduct that impedes purification and reduces the yield. The solvent used in the other process is a water-immiscible solvent that has a higher boiling point than the final product (EDOT), which is usually isolated by fractional distillation under reduced pressure. Since the first purification by fractional vacuum distillation can give a mixture with a purity of about 50% (simultaneously distilled with the solvent), a second fractional vacuum distillation should be carefully carried out to obtain the final product in high purity. Thus, this process is complicated and gives low productivity.

SUMMARY OF THE INVENTION

The object of the present invention is to provide a novel, simple and easy process for preparing 3,4-dialkoxythiophenes of the following chemical formula [1] and 3,4-alkylenedioxythiophenes of the following chemical formula [2] by the decarboxylation of 3,4-dialkoxythiophenedicarboxylic acid of the following chemical formula [3] and 3,4-alkylenedioxythiophenedicarboxylic acid of the following chemical formula [4], respectively, in a water-miscible polar solvent with a lower boiling point than the final product, in the presence of copper catalyst under an oxygen atmosphere.

Another object of the present invention is to provide for the preparation of 3,4-dialkoxythiophenes of the the following chemical formula [1] and 3,4-alkylenedioxythiophenes of the following chemical formula [2] by the decarboxylation of 3,4-dialkoxythiophenedicarboxylic acid of the following chemical formula [3] and 3,4-alkylenedioxythiophenedicarboxylic acid of the following chemical formula [4], respectively, at low temperature in a short reaction time to prevent the formation of a tar-like byproduct.

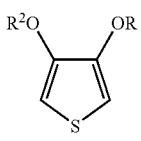

Chemical Formula [1]

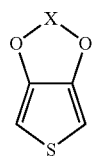

Chemical Formula [2]

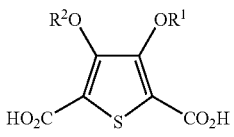

Chemical Formula [3]

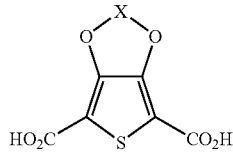

Chemical Formula [4]

In the parent 3,4-dialkoxythiophene of said chemical formula [1] or 3,4-dialkoxythiophene-2,5-dicarboxylic acid of said chemical formula [3], $R^1$ and $R^2$ each represent a straight-chain or branched alky group with 1 to 9 carbon atoms. In the parent 3,4-alkylenedioxythiophene of said chemical formula [2] or 3,4-alkylenedioxythiophene-2,5-dicarboxylic acid of said chemical formula [4] X is optionally substituted by $-(CH_2)_n-$, where n is an integer from 1 to 9.

The process according to the present invention is specifically suitable for preparing 3,4-ethylenedioxythiophene (EDOT; IUPAC name: 2,3-dihydrothieno[3,4-b]-1,4-dioxin) of the following chemical formula [5] and alkyl-substituted compounds of the following chemical formula [6] or 3,4-dimethoxythiophene.

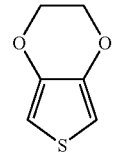

Chemical Formula [5]

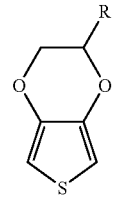

Chemical Formula [6]

In the formulas above, R represents a straight-chain or branched alky group with 1 to 9 carbon atoms.

DETAILED DESCRIPTION OF THE PREFERRED EMBODIMENTS

According to the present invention, the reaction is carried out by suspending the starting material, dialkoxythiophenedicarboxylic acid or alkylenedioxythiophenedicarboxylic acid and copper catalyst in a water-miscible polar solvent with a lower boiling point than the final product. Decarboxylation step is then carried out at elevated temperature that does not exceed 170° C., and the reaction mixture is washed with water to remove solvent. The final product is distilled off at reduced pressure. In general, a single simple vacuum distillation is sufficient to obtain particularly pure product.

More specifically, the process according to the invention is characterized in that dialkoxydithiophenedicarboxylic acid or alkylenedioxythiophenedicarboxylic acid as the starting material is dissolved in a water-miscible polar solvent, and the solution is heated in the presence of copper catalyst under an oxygen atmosphere. If the starting material dialkoxythiophenedicarboxylic acid or alkylenedioxythiophenedicarboxylic acid contains moisture, no additional separate drying process is needed.

More specifically, a water-miscible solvent with a boiling point lower than 225° C. is suitable, and can be selected from among sulfoxides, amides and alcohols with boiling points lower than 225° C. Preferably, dimethylsulfoxide (DMSO), N,N-dimethylformamide (DMF) or ethylene glycol (EG) is used as a solvent.

Decarboxylation is carried out at a temperature of 100° C. to 170° C., and preferably at a temperature of 120° C. to 140° C. At a temperature lower than 100° C., the reaction does not occur, while a tar-like byproduct is formed above 170° C. The catalyst can be a compound containing copper, for example, a copper powder or a copper salt. The preferred catalyst is a copper powder, basic cuprous(cupric) carbonate, cuprous(cupric) sulfate, cuprous(cupric) oxide or cuprous(cupric) hydroxide.

The presence of oxygen in the invention means the reaction can proceed in air as well as under a pure oxygen atmosphere. In particular, the use of a copper salt and/or a copper powder catalyst in the presence of oxygen promotes the decarboxylation. Thus, the reaction is performed by introducing oxygen-containing air or pure oxygen gas into the reaction vessel using a needle. The catalytically active oxygen promotes the decarboxylation step even at a lower temperature in a short reaction time. In the absence of oxygen, decarboxylation is retarded and is not complete even with a prolonged reaction time at an elevated temperature. Under a nitrogen atmosphere without oxygen, it has been observed that decarboxylation barely occurs.

After decarboxylation according to the present invention, purification of the final product from the reaction mixture is carried out according to a conventional work-up process. More specifically, washing the reaction mixture twice with roughly the same amount of water removes the solvent and gives the final product with a purity of 95% or more (by Gas Chromatography). For additional purification, simple distillation in vacuo gives the final product having purity of 99.7% or more as a distillate. In particular, the use of a water-miscible polar solvent simplifies the workup process by making it easy to remove the solvent from the reaction mixture, which in turn makes simple vacuum distillation possible to isolate the product in highly pure product. Due to the use of a water-miscible polar solvent, the reaction by-products can be readily removed and the solvent facilitates washing the reaction vessel after preparation.

In a particularly suitable embodiment, moist dialkoxythiophenedicarboxylic acid is introduced to a water-miscible polar solvent, and removal of moist is unnecessary. Decarboxylation is carried out even in the presence of 1–2% of water.

The present invention will now be explained by a detailed description of exemplary embodiments, with reference to the accompanying Examples, which are given only by way of illustration. It should be obvious to a person with ordinary skill in the art that the scope of the present invention is not limited by these Examples due to the nature of the invention.

EXAMPLES

Example 1

Preparation of EDOT in DMSO in the Presence of a Copper Powder Under Oxygen 3,4-Ethylenedioxythiophene-2,5-dicarboxylic acid (460 g) and a copper powder (46 g) were added to DMSO (1200 g) at room temperature. The reaction mixture was stirred under an oxygen atmosphere for 30 minutes at room temperature and then heated at 120° C. for 6 hours. The reaction mixture was then poured into ice water (1200 mL), and the crude product was extracted with ethyl acetate. After drying over anhydrous sodium sulfate, the solvent was removed by evaporation. The residue was vacuum-distilled at 30 mmHg to give 283 g of 3,4-ethylenedioxythiophene at high purity (99.7% or higher). The purity was confirmed by gas chromatographic analysis (compared to decane as an internal standard). The chemical structure was confirmed by mass analysis and $^1$H-NMR.

Comparative Example 1

The Same Reaction was Performed Under a Nitrogen Atmosphere 3,4-Ethylenedioxy-2,5-thiophenedicarboxylic acid (460 g) and a copper powder (46 g) were added to DMSO (1200 g) at room temperature. The reaction mixture was stirred under a nitrogen atmosphere for 30 minute at room temperature. Sufficient nitrogen was added to the reaction flask so as to completely expel oxygen from inside, and the reaction mixture was heated at 120° C. for 6 hours, but the reaction did not occur. Upon further heating for 10 hours, about 30% of the starting material was converted into product and a tar-like byproduct, while 70% of the starting material still remained in the reaction mixture.

Example 2

Preparation of EDOT in Ethylene Glycol in the Presence of a Copper Powder Under Air 3,4-Ethylenedioxy-2,5-thiophenedicarboxylic acid (460 g) and a copper powder (69 g) were added to ethylene glycol (1400 g) at room temperature. The reaction mixture was stirred under air for 30 minutes at room temperature, and air was continuously introduced into the reaction mixture. The reaction mixture was then heated at 140° C. for 8 hours. After the reaction was complete, the reaction mixture was purified using the same process as described in Example 1 to obtain 3,4-ethylenedioxythiophene (281 g, purity: 98%).

Example 3

Preparation of EDOT in DMF in the Presence of Basic Copper Carbonate Under Air 3,4-Ethylenedioxythiophene-2,5-dicarboxylic acid (230 g) and basic copper carbonate (23 g) were added to DMF (600 g) at room temperature. While air was slowly introduced to the reaction mixture, it as heated at 120° C. for 5 hours. After cooling, the reaction mixture was purified using the same process as described in Example 1 to obtain 3,4-ethylenedioxythiophene (136 g, purity: 97%).

Example 4

Preparation of 34-Dimethoxythiophene Using Copper Catalyst Air (or Oxygen) and DMSO Solvent 3,4-Dimethoxy-2,5-thiophenedicarboxylic acid (232 g) and copper powder (23 g) were added to DMSO (650 g) at room temperature. The reaction mixture was stirred under oxygen atmosphere for 30 minutes at room temperature and then heated at 120° C. for 7 hours. The reaction mixture was then poured into ice water (500 mL), and the crude product was extracted with ethyl acetate. After drying over anhydrous sodium sulfate, the solvent was removed by evaporation. The residue was vacuum-distilled at 50 mmHg to give 127 g of 3,4-ethylenedioxythiophene in high purity (96% or higher). The purity was confirmed by gas chromatographic analysis. The chemical structure was confirmed by mass analysis and $^1$H-NMR.

What is claimed is:

1. A process for preparing 3,4-dialkoxythiophene of the following chemical formula [2].

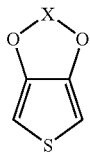

Chemical Formula [2]

which consists of decarboxylating
a parent 3,4-alkylenedioxy-2,5-thiophenedicarboxylic acid of the following chemical formula [4],

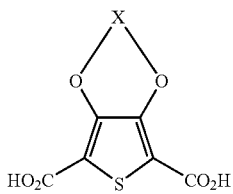

Chemical Formula [4]

wherein X represents an optionally substituted —$(CH_2)_n$—, where n is an integer from 1 to 9, in a water-miscible polar solvent that has a boiling point lower than 225° C. in the presence of copper catalyst under an oxygen atmosphere by removing solvent by washing with water and isolation of the product by simple vacuum distillation.

2. A process according to claim 1, wherein the oxygen atmosphere is either air or pure oxygen gas.

3. A process according to claim 1, wherein the water-miscible polar solvent is a solvent or solvent mixture of two or more solvents selected from a group consisting of sulfoxides, alcohols and amides.

4. A process according to claims 1, wherein the solvent is a solvent or solvent mixture of two or more solvents selected from a group consisting of dimethylsulfoxide, N,N-dimethylformamide and ethylene glycol.

5. A process according to claim 1, wherein the copper catalyst is a catalyst selected from a group consisting of copper powder and copper salt, or a mixture of copper powder and copper salt.

6. A process according to claim 5, wherein the copper salt is selected from a group consisting of basic cuprous (cupric) carbonate, cuprous (cupric) sulfate, cuprous (cupric) oxide and cuprous (cupric) hydroxide.

7. A process according to claims 1, wherein the decarboxylation is performed at a temperature from 100 to 170° C.

8. A process according to claim 7, wherein the decarboxylation is performed at a temperature from 120 to 140° C.

9. A process as in claim 1, the 3,4-dialkoxythiophene is 3,4-dimethoxythiophene.

* * * * *